US008051760B2

(12) United States Patent
Walter

(10) Patent No.: US 8,051,760 B2
(45) Date of Patent: Nov. 8, 2011

(54) MICROTOME HAVING CONCENTRIC OPERATING ELEMENTS FOR CONTROLLING A MOTOR UNIT

(75) Inventor: Roland Walter, Reilingen (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 544 days.

(21) Appl. No.: 12/338,127

(22) Filed: Dec. 18, 2008

(65) Prior Publication Data

US 2009/0165627 A1 Jul. 2, 2009

(30) Foreign Application Priority Data

Dec. 27, 2007 (DE) .................... 20 2007 018 047 U

(51) Int. Cl.
*G01N 1/06* (2006.01)
(52) U.S. Cl. .............. 83/915.5; 83/713; 83/714; 83/717
(58) Field of Classification Search ................ 83/373, 83/403.1, 703, 707, 713–730, 915.5; 318/571, 318/575, 576, 579
See application file for complete search history.

(56) References Cited

U.S. PATENT DOCUMENTS

| | | | |
|---|---|---|---|
| 2,155,523 A | 4/1939 | Bausch et al. | |
| 3,496,819 A * | 2/1970 | Blum | 83/247 |
| 3,785,234 A * | 1/1974 | Sitte | 83/414 |
| 4,691,151 A * | 9/1987 | Behme et al. | 318/571 |
| 5,181,443 A * | 1/1993 | Sitte et al. | 83/72 |
| 6,568,307 B1 | 5/2003 | Günther et al. | |
| 6,598,507 B1 | 7/2003 | Günther et al. | |
| 7,900,545 B2 * | 3/2011 | Schneider | 83/331 |
| 2005/0152760 A1 | 7/2005 | Ranner | |

FOREIGN PATENT DOCUMENTS

| | | |
|---|---|---|
| DE | 199 11 163 | 7/2000 |
| EP | 0 920 613 | 6/1999 |
| JP | 2005077369 | 3/2005 |
| JP | 2005077369 A | 3/2005 |
| WO | 98/04898 | 2/1998 |

* cited by examiner

*Primary Examiner* — Edward Landrum
(74) *Attorney, Agent, or Firm* — Schlee IP International, P.C.; Alexander R. Schlee

(57) ABSTRACT

A microtome for producing thin sections for microscopy is suggested that has a high level of automation and can be operated ergonomically. The microtome has a sectioning knife, a specimen holder, a first and a second motor unit operating the knife, a control system and an operating unit comprising a first and a second operating element. The first operating element controls the relative displacement between the sectioning knife and specimen holder, while the second operating element adjusts the advance rate of the displacement. The first operating element is a rotating ring and the second element is a rotary knob, concentrically within the rotating ring.

8 Claims, 3 Drawing Sheets

US 8,051,760 B2

MICROTOME HAVING CONCENTRIC OPERATING ELEMENTS FOR CONTROLLING A MOTOR UNIT

CROSS-REFERENCE TO RELATED APPLICATION

This application claims the priority of the German Utility Model application DE 202007018047.0 having a filing date of Dec. 27, 2007, the entire content of which is herewith incorporated by reference.

BACKGROUND OF THE INVENTION

The present invention relates to a microtome for producing thin sections for microscopy.

Microtomes are increasingly being equipped with motor units in order to implement the necessary displacement between the sectioning knife and specimen holder, and for the oscillating motion between sectioning knife and specimen holder to generate the thin sections. In this context, a person actuates an operating unit whose signals are processed by a control system so that a first motor unit executes a relative motion between a sectioning knife and a specimen holder in order to bring the two closer to or farther away from one another. The movement speed can be relatively high for the coarse drive mode, until contact takes place between the sectioning knife and a specimen on the specimen holder. When the sectioning knife is in contact with the specimen, the advance must be decreased or halted in order not to destroy the specimen, for example a biological tissue sample. The advance rate for each sectioning motion for generation of the thin sections is often on the order of micrometers, and is thus much lower than for the aforementioned coarse drive mode. This coarse drive mode is usually implemented in different speed increments depending on the distance of the specimen from the sectioning knife. The closer the sectioning knife is to the specimen, the more slowly the further approach should occur so as not to damage the specimen. When controlling this approach, the operator should, if possible, not turn his or her gaze away from the specimen. Operation of the various control parameters, such as coarse drive, fine positioning, and adjustment of the advance rate, with a single hand would be advantageous in this context.

EP 0 920 613 B1 discloses a rotating disc microtome in which at least one specimen holder is mounted on a disc. The oscillating motion between the sectioning knife and specimen holder is produced by rotation of the disc. Relative displacement of the sectioning knife with respect to the specimen holder can be accomplished with a variety of actions: for example, the sectioning knife can be moved horizontally along a base bed, the disc can be moved along the base bed or along the oblique rotation axis of the disc, the disc can be moved vertically on the base bed, and/or the sectioning knife can be moved vertically with the disc placed obliquely.

DE 199 11 163 C1 discloses a microtome in which the displacement of a handwheel is converted, with the aid of electronic positioning elements, into electrical signals that enable control in such a way that a motor unit executes a relative motion between the specimen holder and sectioning knife.

SUMMARY OF THE INVENTION

It is the object of the invention to describe a microtome that has a high level of automation and can be operated ergonomically.

According to the invention, a microtome for producing thin sections for microscopy is provided, having a sectioning knife held on a knife receptacle; a specimen holder for receiving a specimen of which thin sections are to be produced; a first motor unit for relative displacement of the sectioning knife with respect to the specimen holder; a second motor unit for a relative oscillating motion between the sectioning knife and specimen holder in order to produce the thin sections; a control system for applying control to the first motor unit and to the second motor unit; and an operating unit. Said operating unit comprises a first operating element upon the actuation of which a first operating state of the first motor unit can be established, wherein a relative displacement between the sectioning knife and specimen holder at an elevated first displacement speed takes place; and a second operating element upon the actuation of which a second operating state of the first motor unit can be established, wherein a relative displacement at a predetermined advance rate takes place. The first operating element is embodied as a rotating ring that, after being manually rotated and then released, automatically returns to a zero position. In this zero position, the first displacement speed, which corresponds to coarse drive mode, is equal to zero. Relatively good operating safety is achieved with this feature, since if the operator happens to be inattentive or recognizes a hazardous situation, for example that the sectioning knife is coming too close to the specimen, he or she need not perform any active switching motion but must simply remove his or her hand from the operating element. Releasing the operating element causes the zero position to be assumed immediately, in which position the motor unit immediately comes to a halt.

When the rotating ring is deflected through a rotation angle, the magnitude of the first displacement speed is adjusted as a function of the magnitude of the rotation angle. If the operator thus executes a large rotary motion with his or her hand, this is converted by the control system so that the first motor unit assumes a higher displacement speed than in the case of a small rotary motion. Such a procedure also corresponds to the natural intuition of an operator: if the spacing between the sectioning knife and specimen is relatively large, the operator can then, with the aid of a relatively large rotation angle, establish a high speed at which the sectioning knife and specimen are moved toward one another. As the spacing between the sectioning knife and specimen then becomes smaller, the operator intuitively reduces the rotation angle in accordance with the decreased spacing, which results in a low displacement speed.

The second operating element is embodied according to the invention as a rotary knob, concentrically within the rotating ring, having detent positions. Actuation of the rotary knob results in an advance rate as a function of the rotation angle. In the region close to contact between the sectioning knife and specimen, fine positioning can be performed by varying the rotation angle at the rotary knob.

BRIEF DESCRIPTION OF THE DRAWINGS

An exemplifying embodiment of the invention will be described below with reference to the drawings, in which.

DETAILED DESCRIPTION OF THE DRAWINGS

Figure 1:
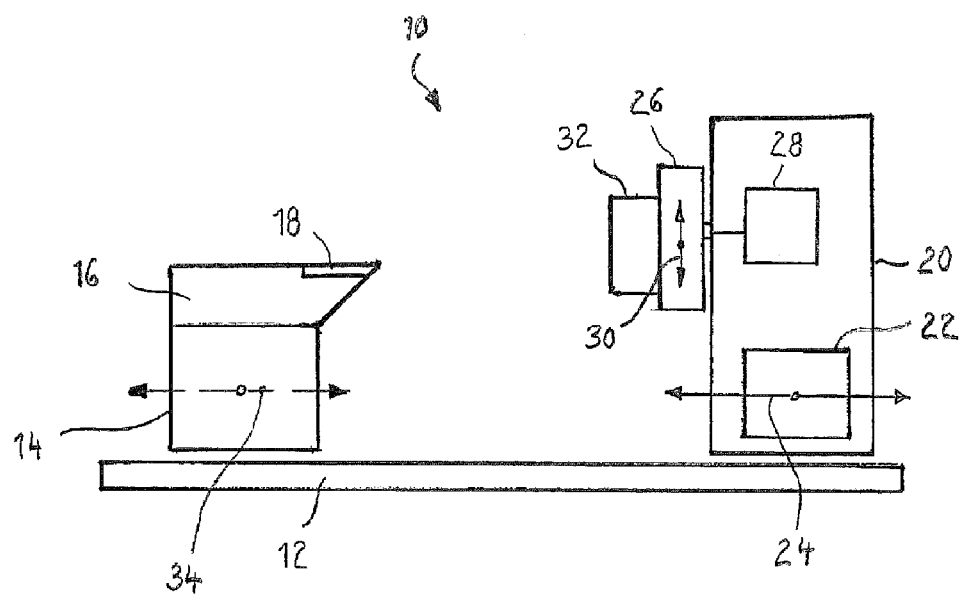
FIG. 1 schematically depicts the configuration of a microtome.

FIG. 1 is a simplified schematic depiction showing, in general, a microtome 10 having a base bed 12 with a knife block 14 arranged thereon, said block carrying a knife receptacle 16. This knife receptacle 16 holds a sectioning knife 18.

Mounted shiftably on base bed 12 is a specimen carriage 20 that can be shifted by a first motor unit 22 in the direction of double arrow 24. Motor unit 22 can be embodied as a stepping motor or a DC motor. Mounted on specimen carriage 20, shiftably in a vertical direction, is a specimen carrier 26 that, by way of a second motor unit 28, can execute oscillating motions in the direction of double arrow 30 so as to produce sections in coaction with the sectioning knife. Secured to specimen holder 26 is a specimen 32, for example a biological sample comprising tissue material, bone, etc., from which thin sections for microscopy are to be produced.

In another variant of the configuration according to FIG. 1, knife block 14 can also be mounted on base bed 12 shiftably in the direction of the dashed-line double arrow 34. Knife block 14 would then be driven by a motor unit similar to motor unit 22 so as to be able to execute a motion relative to specimen holder 26 in a horizontal direction.

In an operating state in which thin sections are not being produced, the spacing between sectioning knife 18 and specimen holder 26, or specimen 32, can be relatively large, for example so that a specimen change can be carried out. For this purpose, the specimen carriage according to FIG. 1 is displaced by motor unit 22 to the right, to an end position. To allow thin sections of specimen 32 to be produced, specimen carriage 22 must be moved toward sectioning knife 18, which requires that a relatively long distance be covered. As long as the spacing between the front edge of sectioning knife 18 and the surface of specimen 32 is large, motion should occur at the highest possible displacement speed. Under the control of an operator, as sectioning knife 18 approaches sample 32 the displacement speed then needs to be reduced and ultimately stopped. Specimen holder 26 then performs oscillating motions under the control of motor unit 28, an advance occurring between each two oscillating motions. This advance rate is preferably on the order of micrometers and can be adjusted, for example, in increments of 10 µm, 20 µm, 30 µm, . . . 100 µm, this advance once again being accomplished by motor unit 22. Under the operator's control, thin sections are then produced from specimen 32, or a favorable sectioning plane within specimen 32 is looked for at an increased advance rate, after which the advance rate is reduced again in order to produce the requisite thin sections.

Figure 2:
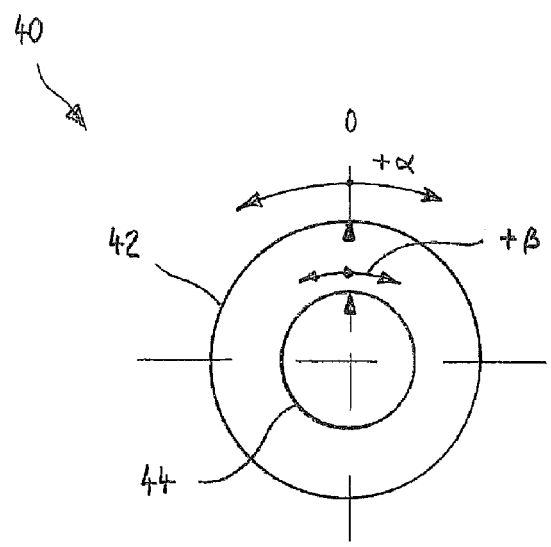
FIG. 2 shows the arrangement of a rotating ring, and of a rotary knob concentric therewith, in an operating unit.

The movement of specimen carriage 20 is carried out by an operator using an operating unit 40 that is depicted in FIG. 2. Operating unit 40 encompasses a rotating ring 42 as a first operating element, and a rotary knob 44 arranged concentrically within rotating ring 42 as a second operating element. Rotating ring 42 and rotary knob 44 generate, with the aid of positioning elements (for example, potentiometers or switches), position signals that are further processed by a control system so that the desired motions are performed by motor unit 22. Rotating ring 42 is equipped with spring elements in such a way that it is preloaded into a zero position "0". When an operator rotates rotating ring 42 clockwise or counter-clockwise through a rotation angle α, the associated positioning element then generates a corresponding signal. When rotating ring 42 is released while in the deflected position, it immediately jumps back, because of the preloaded spring elements, into the zero position, in which a signal characterizing said zero position is delivered. The maximum deflection in both rotation directions is typically 45° in each case, but other maximum rotation angles can also be used. It is advantageous if the operator need not shift his or her grip when deflecting rotating ring 42, but instead the maximum rotation range lies within the natural rotation angle of an operator's wrist. Rotating ring 42 has no detent positions.

Rotary knob 44, on the other hand, does have detent positions into which it snaps; and it remains in that position after said knob is released by the operator. The signal of the positioning element associated with rotary knob 44 controls motor unit 22 in such a way that specimen carriage 20 travels over a predetermined absolute advance distance. Each detent increment is associated with a specific advance, e.g. 5 µm. Fine positioning of specimen 32 at the front edge of sectioning knife 18 can be performed by rotating rotary knob 44 and by displacement over one or more detent increments. Rotary knob 44 is displaceable in both directions, so that specimen carriage 20 can be displaced in a forward direction and reverse direction over the desired advance distance, in accordance with the number of detent increments. Motor unit 28 can be shut off during fine positioning so that specimen holder 26 does not perform an oscillating motion.

In an embodiment, rotary knob 44 can additionally be embodied as a momentary switch, a switching signal being generated when an operator presses on rotary knob 44 perpendicular to the drawing plane in FIG. 2. This switching signal can be used to switch into a predetermined operating mode, for example in order to switch over from the operating mode with fine positioning into an operating mode in which thin sections are produced at a thickness set by way of the advance rate.

Figure 3:
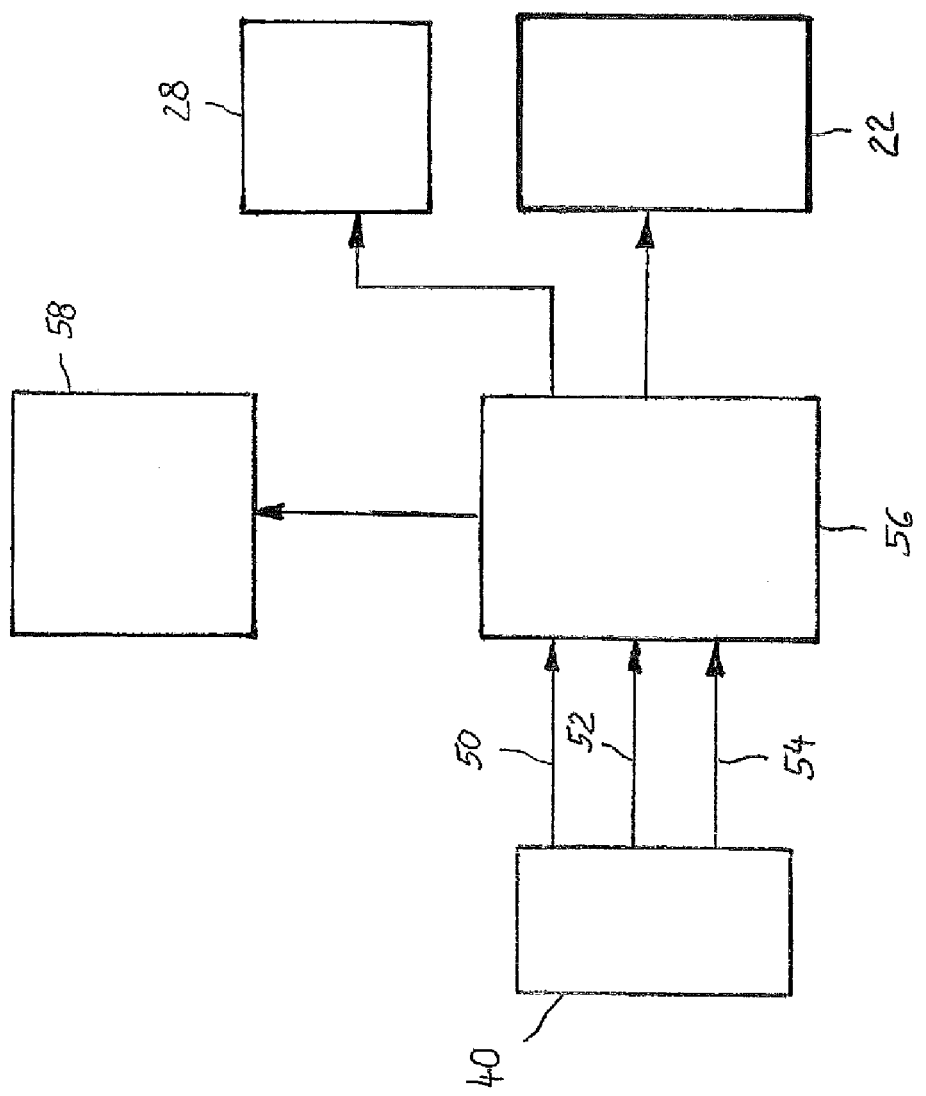
FIG. 3 is a block diagram to explain the control operations.

FIG. 3 shows the device configuration in a block diagram. Signals 50, 52, 54 are generated by operating unit 40 and delivered to a control system 56. Signal 50 maps the rotation angle of rotating ring 42, and contains information regarding angle α, including the zero position. Signal 52 maps the particular detent position of rotary knob 44 that is set, corresponding to rotation angle β. Signal 54 maps the implementation of rotary knob 44 as a pushbutton. As a function of signals 50, 52, 54, control system 56 generates drive signals for motor unit 22 in order to move specimen carriage 20. Control system 56 also generates drive signals for motor unit 28. The operating states that are set are indicated via a display 58.

Figure 4:
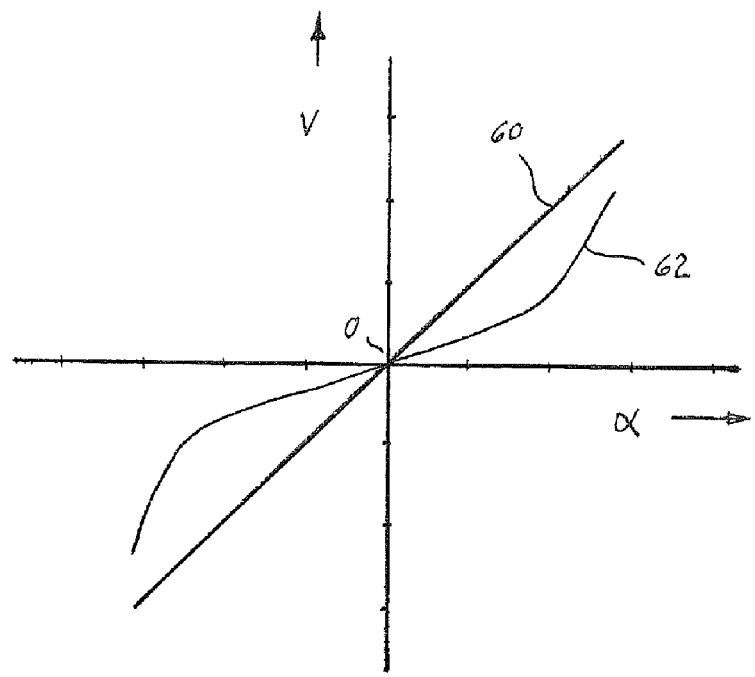
FIG. 4 is a diagram depicting the relationship between displacement speed and rotation angle.

FIG. 4 shows characteristic curves 60, 62 for the relationship between displacement speed v, established with motor unit 22 by way of the control system, and rotation angle α established by an operator on rotating ring 42. Characteristic curve 60 shows a directly proportional behavior for variables α and v. Characteristic curve 62 shows a change in displacement speed v that is progressive with increasing rotation angle α. Characteristic curve 62 allows more accurate positioning around the zero position of rotating ring 42, since the slope of the characteristic curve is less in that region. Characteristic curves 60, 62 show the correlation between α and v, displacement speed v being adjustable in approximately stepless fashion. Alternatively, displacement speed v can also encompass multiple different speed increments, one of the speed increments being selected as a function of rotation angle α, and motor unit 22 being controlled by control system 56 in accordance with a step function.

Further advantageous operating functions can be carried out using rotating ring 42. For example, when an operating state is established in which thin sections are being produced from specimen 32, it may be advantageous to vary the periodic advance rate Δx between two oscillating motions. For example, advance rate Δx can be made relatively large in order to arrive at a favorable sectioning plane within the specimen, whereupon advance rate Δx is made smaller again in order to generate the thin sections at the requisite thickness corresponding to advance rate Δx. In order to implement this operating function, upon displacement of rotating ring 42 through a rotation angle +α or −α, advance rate Δx is increased or decreased by a value dependent on rotation angle α, for example increased or decreased by 10 μm, 20 μm, or 30 μm, until rotating ring 42 is released again by the operator and is moved by spring action back into its zero position. Once it has arrived in this zero position, the advance rate Δx that is thereby established—which if applicable is indicated via display 58—is maintained. This function is also referred to as a trim step function.

Figure 5:
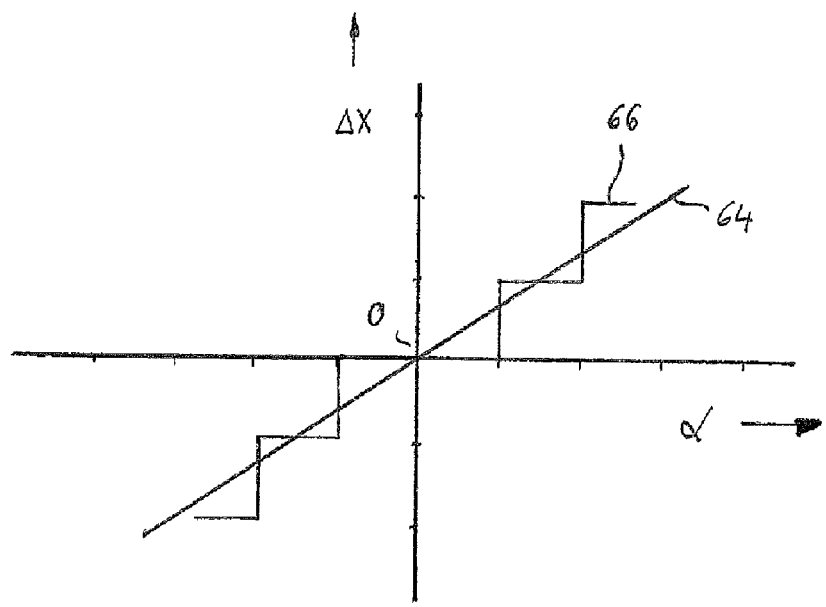
FIG. 5 is a diagram showing the adjustment of advance rate as a function of the rotation angle of the rotary ring, for a further operating state.

FIG. 5 shows, in this connection, a diagram and the correlation between advance rate Δx and rotation angle α; characteristic curve 64 shows a directly proportional correlation, and characteristic curve 66 a stepped correlation. Signal 54 of rotary knob 44, in its function as a pushbutton, can be used to switch the operating mode of rotating ring 42 from the mode shown in FIG. 4 to the mode shown in FIG. 5, and vice versa. The operating mode that is set is indicated, along with the current advance rate Δx as well as further operating parameters, on display 58.

Numerous variants are possible as embodiments of the invention. For example, motor unit 22 can be arranged in knife block 14 in order to displace the latter with respect to specimen holder 26. The function of rotary knob 44 as a pushbutton can encompass a double-click function in order to incorporate further operating functions. For example, an operating function can be established in which the modification of the periodic advance rate Δx is effected with the aid of the rotary knob. Operating unit 40 can be laid out differently for left-handers and for right-handers.

A number of advantages are achieved with the invention. Operating unit 40 can be operated by an operator using a single hand; essential motion functions for a microtome can be adjusted with one-hand operation. Operation is simple and logical, with no need for the operator to have visual contact with operating unit 40. Operation using rotating ring 42 and rotary knob 44 is easy for an operator to learn. A high level of safety is achieved, since a release of rotating ring 42 is immediately converted into a stoppage of the feed motion, so that the risk of destroying the specimen is reduced. The operator can operate the rotating ring and rotary knob intuitively, both for coarse drive mode in which a relatively large distance must be covered, and during fine positioning with the aid of the rotating ring and rotary knob.

LIST OF REFERENCE NUMERALS

10 Microtome
12 Base bed
14 Knife block
16 Knife receptacle
18 Cutting knife
20 Specimen carriage
22 First motor unit
24 Double arrow
26 Specimen carrier
28 Second motor unit
30 Double arrow
32 Specimen
34 Dashed-line double arrow
40 Operating unit
42 Rotating ring
44 Rotary knob
50, 52, 54 Signals
α Rotation angle of rotating ring
β Rotation angle of rotary knob
56 Control system
58 Display
60, 62 Characteristic curves
v Displacement speed
Δx Advance rate
64, 66 Characteristic curves

The invention claimed is:

1. A microtome for producing thin sections for microscopy, having
   a sectioning knife held on a knife receptacle;
   a specimen holder for receiving a specimen of which thin sections are to be produced;
   a first motor unit for relative displacement of the sectioning knife with respect to the specimen holder;
   a second motor unit for a relative oscillating motion between the sectioning knife and specimen holder in order to produce the thin sections;
   a control system for applying control to the first motor unit and to the second motor unit; and
   an operating unit, said operating unit comprising:
      a first operating element upon the actuation of which a first operating state of the first motor unit can be established, wherein a relative displacement between the sectioning knife and specimen holder at an elevated first displacement speed takes place; and
      a second operating element upon the actuation of which a second operating state of the first motor unit can be established, wherein a relative displacement at a predetermined advance rate takes place,
   wherein the first operating element is embodied as a rotating ring that, after a manual rotation, upon release automatically returns into a zero position wherein the displacement speed is equal to zero, the magnitude of the first displacement speed being adjustable, upon a deflection of the rotating ring through a rotation angle, as a function of said rotation angle; and
   the second operating element is embodied as a rotary knob, concentrically within the rotating ring, having detent positions, the advance rate being adjustable as a function of the rotation angle of the rotary knob.

2. The microtome according to claim 1, wherein the rotating ring is displaceable in both rotation directions proceeding from the zero position, the forward motion of the first motor unit being associated with the one rotation direction, and the reverse motion of the motor unit with the other rotation direction.

3. The microtome according to claim 1, wherein the first displacement speed is adjustable in approximately stepless fashion.

4. The microtome according to claim 3, wherein the first displacement speed is proportional to the rotation angle of the rotating ring.

5. The microtome according to claim 1, wherein the first displacement speed encompasses multiple different speed increments, one of the speed increments being selectable as a function of the rotation angle.

6. The microtome according to claim 1, wherein the rotary knob of the second operating element has detent positions and is displaceable by one or more detent increments in both rotation directions, the one rotation direction corresponding to a forward motion of the first motor unit and the other rotation direction to a reverse motion of the first motor unit.

7. The microtome according to claim 1, wherein in an operating state in which thin sections of the specimen are being produced, the advance rate for each thin section is raised or lowered as a function of the rotation angle by rotation of the rotating ring, until the rotating ring once again assumes its zero position after being released.

8. The microtome according to claim 1, wherein the rotary knob is additionally embodied as a momentary switch, upon the actuation of which a change in operating mode occurs.

* * * * *